United States Patent [19]

McEvoy et al.

[11] 4,342,689

[45] Aug. 3, 1982

[54] ω-HETEROAROYL(PROPIONYL OR BUTYRYL)-L-PROLINES

[75] Inventors: Francis J. McEvoy, Pearl River, N.Y.; William B. Wright, Jr., Woodcliff Lake, N.J.; Gary H. Birnberg, Spring Valley; Jay D. Albright, Nanuet, both of N.Y.

[73] Assignee: American Cyanamid Company, Stamford, Conn.

[21] Appl. No.: 242,765

[22] Filed: Mar. 11, 1981

Related U.S. Application Data

[62] Division of Ser. No. 144,741, Apr. 28, 1980, Pat. No. 4,299,769.

[51] Int. Cl.$^3$ .............................................. C07D 405/06
[52] U.S. Cl. ...................... 260/326.34; 260/326.22; 424/274; 544/107; 544/372; 546/197
[58] Field of Search ..................................... 260/326.34

[56] References Cited

U.S. PATENT DOCUMENTS

| | | | |
|---|---|---|---|
| 4,091,024 | 5/1978 | Ondetti | 260/326.25 |
| 4,116,962 | 9/1978 | Ondetti et al. | 260/326.25 |
| 4,154,934 | 5/1979 | Bernstein et al. | 260/326.25 |
| 4,154,946 | 5/1979 | Ondetti et al. | 260/326.25 |
| 4,226,775 | 10/1980 | McEvoy et al. | 260/326.43 |

*Primary Examiner*—Alton D. Rollins
*Attorney, Agent, or Firm*—Edward A. Conroy, Jr.

[57] ABSTRACT

This disclosure describes novel substituted ω-heteroaroyl(propionyl or butyryl)-L-prolines and the esters and cationic salts thereof which are useful as hypotensive agents in mammals.

10 Claims, No Drawings

ω-HETEROAROYL(PROPIONYL OR BUTYRYL)-L-PROLINES

CROSS REFERENCE TO RELATED APPLICATION

This application is a division or our copending application Ser. No. 144,741, filed Apr. 28, 1980, now U.S. Pat. No. 4,299,769, issued Nov. 10, 1981.

BRIEF SUMMARY OF THE INVENTION

This invention relates to new organic compounds and, more particularly, is concerned with novel ω-heteroaroyl(propionyl or butyryl)-L-prolines and esters thereof which may be represented by the following general formulae:

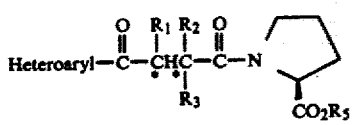

I

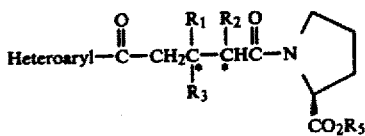

II

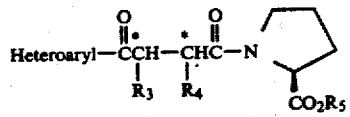

III wherein $R_1$ is hydrogen or alkyl having from 1-3 carbon atoms; $R_2$ is hydrogen or alkyl having from 1-3 carbon atoms; $R_3$ is mercapto, formylthio, benzoylthio, alkanoylthio having from 2-4 carbon atoms or moieties of the formulae:

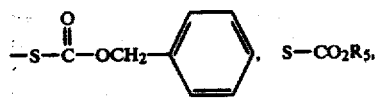

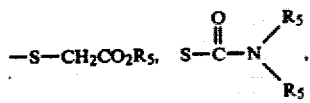

$R_4$ is hydrogen or alkyl having from 1-4 carbon atoms; $R_5$ is hydrogen or alkyl having from 1-4 carbon atoms; and heteroaryl is selected from the group consisting of moieties of the formula:

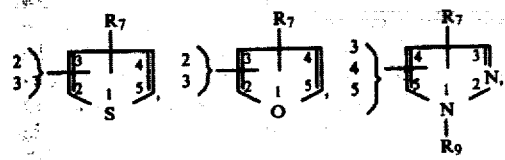

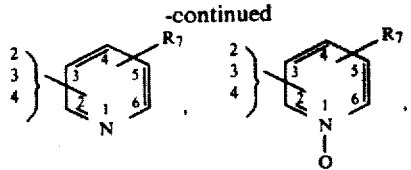

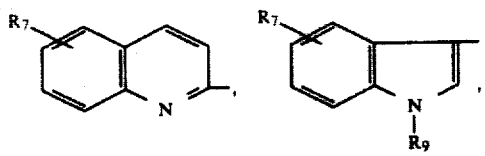

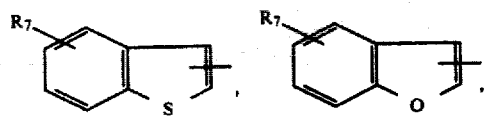

wherein $R_7$ is hydrogen, fluoro, chloro, bromo or alkyl having from 1-4 carbon atoms and $R_9$ is hydrogen or alkyl having from 1-4 carbon atoms; and the pharmacologically acceptable cationic salts thereof when $R_5$ is hydrogen.

The novel compounds of the present invention possess asymmetric carbon atoms (which are indicated by asterisks) and thus exist in diastereoisomeric forms.

DETAILED DESCRIPTION OF THE INVENTION

The novel ω-heteroaroyl(propionyl or butyryl)-L-prolines and esters thereof of the present invention are generally obtainable as white to yellow solids having characteristic absorption spectra or are obtained as white or yellow crystals with characteristic melting points and absorption spectra. They are generally soluble in many organic solvents such as lower alkanols, tetrahydrofuran, dioxane, chloroform and the like.

Also included within the purview of the present invention are the cationic salts of the compounds of the above general formulae wherein $R_5$ is hydrogen. The useful pharmaceutically acceptable salts of the compounds wherein $R_5$ is hydrogen are those with pharmacologically acceptable metal cations, ammonium, amine cations, or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, copper, iron and in particular zinc, are within the scope of the invention. Pharmacologically acceptable amine cations are those derived from primary, secondary or tertiary amines such as mono-, di- or trimethylamine, ethylamine, dibutylamine, triisopropylamine, N-methylhexylamine, decylamine, allylamine, cyclopentylamine, dicyclohexylamine, mono- or dibenzylamine, α- or β-phenylethylamine, ethylenediamine, and arylaliphatic amines containing up to and including 18 carbon atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 1,4-dimethylpiperazine, and the like, as well as amines containing water-solubilizing or hydrophilic groups, e.g. mono-, di-, or triethanolamine, N-butylethanolamine, 2-amino-1-butanol, 2-amino-2-ethyl-1,3-propanediol, tris(hydroxymethyl)aminomethane, N-phenylethanolamine, galactamine, N-methylglucosamine, ephedrine, phenylephrine, epinephrine, procaine, and the like. Examples of suitable pharmacologically acceptable quaternary ammonium cations are tetramethylammonium, tetraethylammonium, benzyltrimethylammonium, phenyltriethylammonium, and the like.

Angiotensin II is a powerful vasoconstrictor agent that has been implicated as the main causative agent in the etiology of renovascular hypertension. Angiotensin II is formed from angiotensin I by the action of angiotensin converting enzyme. Angiotensin I is a biologically inert decapeptide cleaved from the blood protein angiotensinogen by the action of the enzyme renin [Oparil et al., New England J of Med., 291, 389–457 (1974)]. Angiotensinogen and renin are also biologically inert. Agents that inhibit angiotensin converting enzyme can therefore counteract the pressor efect of angiotensin I since this is due only to its conversion to angiotensin II. These agents can be used therapeutically in the treatment of forms of renovascular and malignant hypertension as well as other forms of angiotensin dependent hypertension [Gavras, et al., New England J. of Med. 291, 817 (1974)].

The novel compounds of this invention inhibit angiotensin converting enzyme and thus inhibit the conversion of angiotensin I to angiotensin II and are therefore useful in reducing hypertension, especially angiotensin related hypertension in various mammalian species. The activity of the novel compounds of this invention as hypotensive agents was established in two systems which measure their ability as angiotensin converting enzyme inhibitors; by utilizing a spectrophotometric assay of the compounds in vitro and by the measurement of the blood pressure lowering effect of the compounds in the aorta-coarcted renal hypertensive rats.

Spectrophotometric Assay for Angiotensin Converting Enzyme Inhibitors

The in vitro activity for inhibition of the angiotensin converting enzyme (ACE) was measured by the method of Cushman, D. W. and Cheung, H. S., Biochem. Pharmacol., 20, 1637–1648 (1971), using benzoyl-glycyl-histidyl-leucine as the substrate. The reaction mixture consisted of 50 μl. of potassium phosphate (500 mM., pH 10.2), 30 ml. of sodium chloride (2500 mM.), 25 μl. of substrate (50 mM.), 30 to 50 μl. of the crude extract of ACE, 10 μl. of test compound (2.5 mM.) or vehicle and a suitable amount of distilled water to give a total volume of 250 μl. This reaction mixture was incubated for 30 minutes at 37° C. and the reaction was then terminated by the addition of 250 μl. of 1 N hydrochloric acid. The hippuric acid was then extracted with 1.5 ml. of ethyl acetate by vortex mixing for 15 seconds. After centrifugation, one ml. of th ethyl acetate layer was pipetted into a new tube and vaporated to dryness. The extracted hippuric acid was then dissolved in one ml. of water and the amount of this acid was then measured by its absorbance at 228 nm. The ACE was extracted from rabbit lung acetone powder (Pel-Freez Biol. Inc.) by blending 5 g. of the powder in 50 ml. of phosphate buffer (50 mM., pH 8.3) and then centrifuging at 40,000 g for 40 minutes. The supernatant was then kept at 5° C. and used as the enzyme source. The activity of the ACE inhibitor was calculated as the percent inhibition of ACE activity compared to the control value of that particular assay. A full dose-response inhibitory curve is then performed to determine the $IC_{50}$ value which may be defined as the molar concentration of a compound that will inhibit the ACE activity by 50%. Representative compounds of the present invention and their corresponding $IC_{50}$ values as determined by the above procedure are set forth in Table I below.

TABLE I

| Angiotensin Converting Enzyme Inhibitors | |
|---|---|
| Compound | $IC_{50} (10^{-7} M)$ |
| 1-[3-(Acetylthio)-3-(2-thenoyl)-propionyl]-L-proline | 2.56 |
| 1-[3-(Acetylthio)-3-(5-bromo-2-thenoyl)propionyl]-L-proline | 1.09 |
| 1-[3-(Acetylthio)-3-(5-chloro-2-thenoyl)propionyl]-L-proline | 1.08 |
| 1-[3-(Acetylthio)-3-(benzo[b]-thien-3-ylcarbonyl)propionyl]-L-proline | 1.39 |
| 1-[3-(Acetylthio)-3-(2-furoyl)-propionyl]-L-proline | 6.75 |
| 1-[3-(Acetylthio)-3-(2-benzofur-anylcarbonyl)propionyl]-L-proline | 0.74 |
| 1-[3-(Acetylthio)-3-(benzo[b]-thien-2-ylcarbonyl)-2-methyl-propionyl]-L-proline | 210 |

Measurement of Arterial Blood Pressure in Aorta-Coarcted Renal Hypertensive Rats Male, Sprague-Dawley normotensive rats, weighing 300–325 g. (Charles River Breeding Lab. Inc., Wilmington, Mass.) were maintained on Purina Laboratory Chow and tap water ad libitum for 1–7 days before use. Hypertension was induced by complete ligation of the aorta between the origin of the renal arteries, according to the method of Rojo-Ortega, J. M. and Genest, J., A Method for Production of Experimental Hypertension in Rats, in Can. J. Physiol. Pharmacol. 46, 883–885 (1968), with modifications of the surgical procedures. Thus, rats were anesthetized with methohexitol sodium at 66 mg./kg. of body weight, intraperitoneally and were laid on their right side. An incision was made just below the rib cage on their left side. With a cotton-tip swab, the fat was gently pushed back to expose the left kidney. The kidney was held gently between the thumb and the forefinger outside of the body cavity. The aorta was completely ligated between the origin of the renal arteries with a No. −000 silk suture. Care was taken to avoid the occlusion of the mesenteric artery. The wound was then closed in two layers using a 4–0 polyglycolic acid suture on the muscle and wound clips on the skin. The wound is then sprayed with No. 3 thimerosal aerosol. Following this surgery, the rats were returned to their cages and provided with Purina Laboratory Chow and water ad libitum. Six days after surgery, the conscious rats were restrained on rat boards with elastic tape. The neck area was locally anesthetized by subcutaneous infiltration of 2% lidocaine. After the trachea was cannulated and the rat respired spontaneously, the carotid artery was isolated and cannulated with a nylon catheter (inside diameter −0.015", outside diameter 0.030") was connected to a Statham P23Gb pressure transducer—Gold Brush recorder (Model 2400) for monitoring blood pressure. The test compounds were dissolved in a small amount of ethanol and then diluted to the desired concentration with saline. Both the solution of the test compound and the vehicle alone were administered orally and run parallel in each experiment. The following representative compounds of the present invention were considered active when tested by this procedure:

1-[3-(Acetylthio)-3-(2-thenoyl)propionyl]-L-proline
1-[3-(Acetylthio)-3-(5-bromo-2-thenoyl)propionyl]-L-proline
1-[3-(Acetylthio)-3-(5-bromo-2-thenoyl)propionyl]-L-proline
1-[3-(Acetylthio)-3-(benzo[b]thien-3-yl-carbonyl)propionyl]-L-proline
1-[3-(Acetylthio)-3-(2-furoyl)propionyl]-L-proline.

The novel compounds of the present invention have thus been found to be highly useful for lowering elevated blood pressure in mammals when administered in amounts ranging from about one mg. to about 1000 mg. per kilogram of body weight per day. A preferred dosage regimen for optimum results would be from about 10 mg. to about 300 mg. per kilogram of body weight per day. The dosage regimen may be adjusted to provide the optimum therapeutic response. For example, several divided doses may be administered daily or the dose may be proportionally reduced as indicated by the exigencies of the therapeutic situation. The active compounds are preferably administered orally but may be administered in any convenient manner such as by the intravenous, intramuscular or subcutaneous routes.

Compositions according to the present invention having the desired clarity, stability and adaptability for parenteral use are obtained by dissolving or suspending the active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid polyethylene glycols which are soluble in both water and organic liquids and which have molecular weights of from about 200 to 1500. Although the amount of active compound dissolved or suspended in the above vehicle may vary the amount of active substance in the composition is such that dosage in the range of about 10 to 500 mg. of compound is obtained. Although various mixtures of the aforementioned non-volatile polyethylene glycols may be employed, it is preferred to use a mixture having an average molecular weight of from about 200 to about 400.

In addition to the active compound, the parenteral solutions or suspensions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens and thimerosal. As a practical matter, it is also convenient to employ antioxidants, such as, for example, sodium bisulfite, sodium metabisulfite and sodium formaldehyde sulfoxylate. Generally, from about 0.05 to about 0.2% concentrations of antioxidant are employed.

The active compounds of the present invention may be orally administered, for example, with an inert diluent or with an assimilable edible carrier, or they may be enclosed or hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder such as gum tragacanth, accia, corn starch or gelatin; excipients such as dicalcium phosphate; a disintegrating agent such as corn starch, potato starch, alginic acid and the like; a lubricant such as magnesium stearate; and a sweetening agent such as sucrose or lactose may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or suspension may contain the active compound, sucrose as a sweetening agents, methyl and propyl parabens as preservatives, a dye and flavoring such as cherry or orange flavor. Of course, any material used in preparing any dosage unit form should be pharmaceutically pure and substantially non-toxic in the amounts employed.

The novel compounds of formula (III) of the present invention may be prepared in accordance with the following reaction scheme:

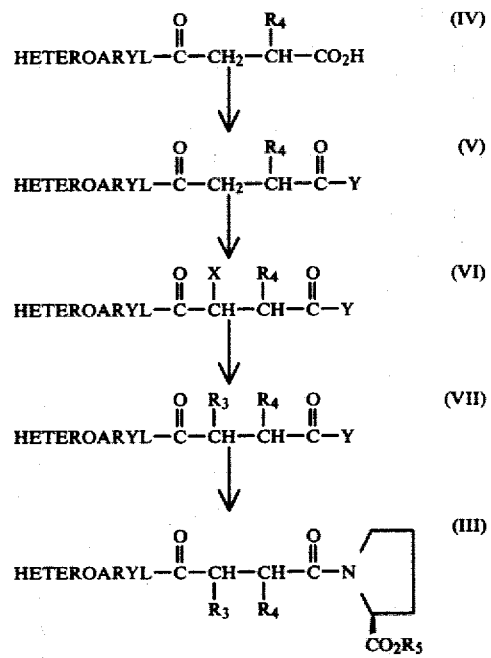

wherein $R_3$, $R_4$, $R_5$ and HETEROARYL are as hereinbefore defined; X is chloro, bromo, iodo, —S—R or —SO$_2$R; wherein R is alkyl having 1–4 carbon atoms, phenyl, p-tolyl, benzyl, p-methoxybenzyl and the like;

and Y is the carbonyl activating residue of a peptide coupling reagent or a group of the formulae:

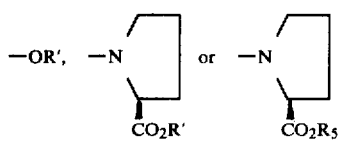

wherein R' is hydrogen, alkyl having 1–4 carbon atoms, phenyl, p-tolyl, p-methoxybenzyl, 2,4,6-trimethylbenzyl, trimethylsilyl, 2-trimethylsilylethyl and the like or a suitable carbonyl protecting group; and $R_5$ is as hereinbefore defined.

In accordance with the above reaction scheme, the carboxyl group of an appropriately substituted ω-heteroaroylalkanoic acid (IV) is converted to a carbonyl activated derivative (V) or in accordance with the reaction scheme, derivatives (VI) (Y=OH) and (VII) (Y=OH) are converted to carbonyl activated derivatives. The carbonyl activated derivatives of (V), (VI) and (VII) are prepared by reaction of the free acids under standard reaction conditions for activating the carboxyl groups of N-protected aminoacids. For example, mixed anhydrides are prepared in situ by treatment of the free acids with bases such as trialkylamines (triethylamino and the like), N-methylmorpholine, pyridine, N-methylpiperidine and the like to give the amine salts which are reacted with lower alkyl chloroformates such as ethyl chloroformate, t-butyl chloroformate, isobutyl chloroformate, benzyl chloroformate, trityl chloroformate and the like. Alternatively, the free acids are reacted with N,N'-carbonyldiimidazole or related peptide coupling reagents such as N,N'-carbonyl-1,2,4-triazole to form activated carbonyl derivatives. Derivatives where Y is O-hydroxysuccinimide or O-hydroxyphthalimide are prepared by reaction of the free acids with N-hydroxysuccinimide or N-hydroxyphthalimide in the presence of a carbodiimide such as N,N-dicyclohexylcarbodiimide. Derivatives wherein Y is a residue of a peptide coupling reagent or an activated ester are reacted with L-proline or L-proline derivatives under conventional coupling conditions.

The amides are obtained by reacting an acid halide of (IV) or preferably a carbonyl activated derivative (V) with L-proline or an ester of L-proline such as an alkyl ($C_1$–$C_4$) ester, benzyl ester, 2,4,6-trimethylbenzyl ester and other L-proline derivatives with a protected acid function which is removed in a later step. The reaction conditions for the formation of the carboxyl activated derivatives and conditions for coupling to L-proline or L-proline derivatives, such as time, temperature, solvents, etc. are well known in the art. In general the reactions are carried out at 0° C. to 50° C. in solvents such as tetrahydrofuran, dioxane, N,N-dimethylformamide, dimethylsulfoxide, toluene, acetonitrile and the like for 1-24 hours.

Further elucidation of the meaning of the terms employed herein is afforded by the following table wherein typical peptide coupling reagents are listed in the left column and the corresponding carbonyl activating residues are listed in the right column:

| Reagent | —Y |
|---|---|
| N-hydroxyphthalimide | 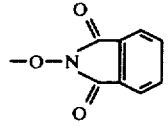 |
| dicyclohexylcarbodiimide | 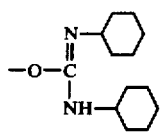 |
| N,N'-carbonyldiimidazole |  |
| benzyl chloroformate | 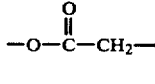 |
| N-hydroxysuccinimide | 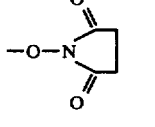 |
| activated ester | —S—Aryl |
| mixed anhydride | 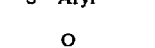 |
|  | 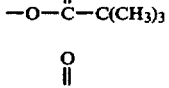 |
|  | —$SO_2$—Aryl |

Numerous other peptide coupling reagents are available and well known to the art such as unsaturated ethers, α-chlorovinyl ethyl ether, ethoxyacetylene, ketenimines and ketenes, ynamines, acyloxyphosphonium ions, EEDQ, silicon tetrachloride, 1,2-oxazolium salts, and the like. These all provide a carbonyl activating residue (-Y) and may be readily used for the conversion of (VI) to (V) when Y is to be a "carbonyl activating residue of a peptide coupling reagent". The reaction conditions for such conversions are well known in the art and may be readily found in such literature references as SYNTHESIS, Sept. 1972, pages 453–463 by Klausner and Bodansky.

The conversion of the intermediates (V) to the corresponding 3-(X-substituted)propionic acid derivative (VI) wherein X consists of the hereinabove defined leaving groups is readily achieved by conventional methods well known in the art. For example, the chloro, bromo and iodo derivatives may be prepared by treating a compound of formula (V) with a halogenating agent such as chlorine, bromine, N-iodosuccinimide, and the like in a solvent such as chloroform, carbon tetrachloride, acetic acid or dioxane at 25°–75° C. for 12–24 hours. Those compounds wherein X is —S—R may be obtained from the halo derivatives by treatment with an alkali metal mercaptide under standard conditions. The corresponding derivatives wherein X=$SO_2R$ may be obtained by oxidation of the corresponding mercapto derivatives with oxidizing agents such as meta-periodic acid and the like in an inert solvent at 10°-100° C. for 1-24 hours. As desired, the ω-heteroaroylalkanoic acids (IV) may be coupled to an L-proline derivative

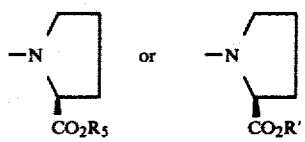

to give intermediates (V) which are then converted to products (III) through intermediates (VI) and (VII). Alternatively, intermediates (V) wherein Y is a carboxyl protecting group may be converted to intermediates (VI) and (VII) at which point the protecting group may be removed and the intermediates (VI) or (VII) (Y=OH) coupled to L-proline or L-proline derivatives.

The ω-heteroaroylalkanoic acids (IV) wherein $R_4$ is other than hydrogen have one asymmetric carbon atom and the D and L isomers may be prepared by resolution of the racemic mixture. Activation of the carboxyl group of the resolved isomers then gives compounds of structure (V) wherein the carbon atom bearing the $R_4$ group has either the D or the L configuration. Conversion of the resolved compounds of structure (V) to the reactive intermediates (VI) gives compounds which are diastereoisomers. Each diastereoisomer may then be converted to compounds of structure (VII) as shown in the reaction scheme. Alternatively, racemic compounds of structure (IV) wherein $R_4$ is lower alkyl may be coupled to L-proline or L-proline derivatives to give compounds of structure (V) which exist as diastereoisomeric forms and may be separated by conventional means. For example, the diastereoisomeric forms of 1-[3-(2-thenoyl)-2-methylpropionyl]-L-proline may be separated by preferential crystallization of one diastereoisomer and isolation of the other diastereoisomer from the mother liquors. In this manner diastereoisomeric forms of structural type (VI) may be prepared and converted to the compounds of structure (III) which are inhibitors of the angiotension converting enzyme. The reactive intermediates (VI) are reacted with the anion of a thioacid of formula

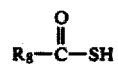

wherein $R_8$ is phenyl, alkyl having up to 3 carbon atoms or other thiolating reagents (H—$R_3$). Suitable anions of thioacids and thiolating reagents useful in the displacement reaction are those from alkali metals ($K^+$, $Na^+$), alkaline earth metals such as calcium and magnesium, and organic bases such as ammonia, trialkylamines, and the like. Removal of the acyl group by reaction with hydroxylamine, ammonium hydroxide or dilute inorganic bases gives the compounds of structure (III) wherein $R_3$ is mercapto. Under appropriate conditions intermediates (VI) and (VII) wherein X is —S—R and Y is

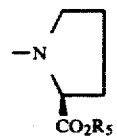

may be converted directly to products (III) wherein $R_3$ is —SH by removal of a thio protecting group. For example, derivatives wherein R is a thio protecting group such as t-butyl, p-methoxybenzyl, $PhCH_2O_2CS$— and the like may be deblocked under acidic conditions [HBr-HOAc, $CF_3CO_2H$, $(CF_3CO_2)_2Hg$ and the like] known to the art.

Derivatives (VII) wherein Y is

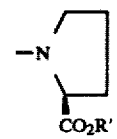

and $R_3$ is as previously defined and R' is a carboxyl protecting group may be converted to product (III) ($R_5$=H) by removal of the carboxyl protecting group under conventional conditions. In general carboxyl protecting groups which are removed under acidic conditions are preferred. For example, t-butyl esters are cleaved by treatment with trifluoroacetic acid or aqueous trifluoroacetic acid at 0° C. to 50° C. for 1-24 hours. Trimethylsilyl and 2-trimethylsilylethyl are removed under conventional conditions known to the art. The reactions illustrated in the reaction scheme may be carried out with esters ($R_5$=lower alkyl) to give the products (III) wherein $R_5$ is lower alkyl. In the products (III) (wherein $R_5$ is tert-butyl) the ester group may be removed in the presence of trifluoroacetic acid to give the free acid derivatives of (III).

The novel compounds of formula (I) of the present invention may be prepared in accordance with the following reaction scheme:

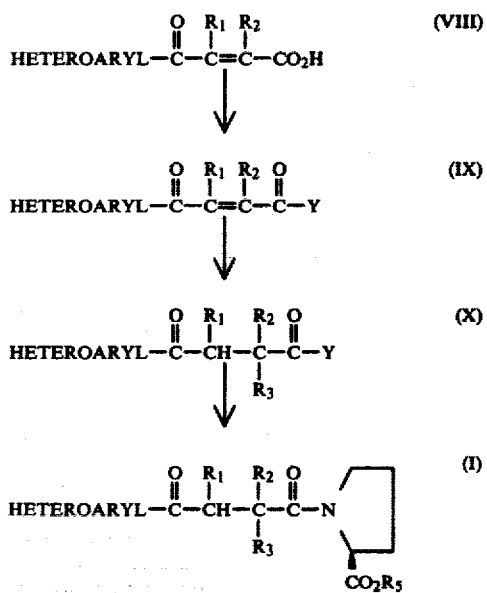

and the novel compounds of formula (II) of the present invention may be prepared in accordance with the following reaction scheme:

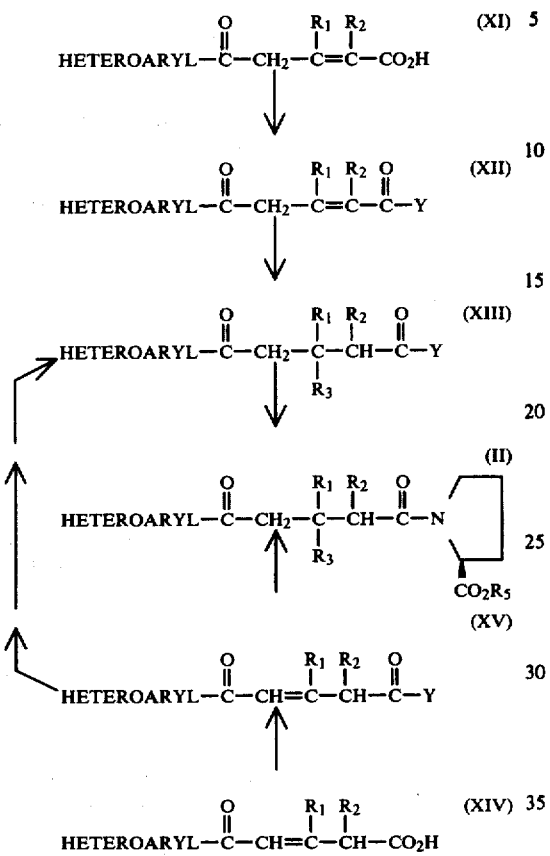

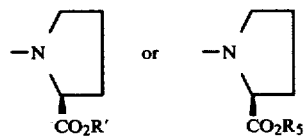

wherein $R_1$, $R_2$, $R_3$, $R_5$, HETEROARYL and Y are as hereinbefore defined. In accordance with the above reaction schemes, an appropriately substituted ω-heteroaroylacrylic acid (VIII), ω-heteroaroylcrotonic acid (XI) or 3-heteroaroyl-3-butenoic acid (XIV) is converted to a carbonyl activated derivative (IX), (XII) or (XV). The reaction conditions for the formation of such carbonyl activated derivatives such as time, temperature, solvents, etc. are well known in the art and are hereinbefore discussed for the conversion of (IV) to products (III). The carboxyl activated derivatives (IX), (XII) and (XV) are prepared by treatment of the free acids (VIII), (XI) or (XIV) with peptide coupling reagents as hereinbefore discussed. (See table of carbonyl activating residues).

Derivatives (IX), (XII) or (XV) wherein Y is a residue of a peptide coupling reagent or an activated ester are reacted with L-proline or an L-proline derivative of the formulae:

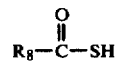

wherein R' and $R_5$ are as previously defined to give intermediates containing a double bond in conjugation with a carbonyl group. The intermediates (IX), (XII) and (XV) are reacted with a thiolating reagent which gives the products (I) or (II) directly or intermediates (X) or (XIII) convertible into products (I) or (II). The position of the double bond determines the direction of the 1,4-addition of the thiolating reagent as shown in the reaction scheme. Thiolating reagents add 1,4 to the ketone carbonyl of intermediates (VIII), (IX), (XIV) and (XV) while addition occurs 1,4 to the carboxyl group in derivatives (XI) and (XII). Suitable thiolating reagents are H₂S, H—S—C(CH₃)₃, and H—R₃ wherein $R_3$ is as hereinbefore defined. Preferred reagents are hydrogen sulfide or a thiolating agent of the formula:

$$R_8-\overset{O}{\underset{\|}{C}}-SH$$

wherein $R_8$ is phenyl or alkyl having up to 3 carbon atoms.

The preferred conditions for the addition of a thiolating reagent are reaction in inert solvents such as chloroform, dichloromethane, carbon tetrachloride, dimethylformamide, tetrahydrofuran, dioxane, acetonitrile, toluene, lower alkanols and the like at 0° C. to 100° C. for 1-24 hours. Conversion of compounds (X) and (XIII) wherein Y is a group of the formula:

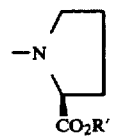

and R' is a carboxyl protecting group as previously defined is carried out by removal of the protecting group to give products (I) and (II) wherein $R_5$=H. Carboxyl protecting groups which are removed under acidic conditions are preferred. The reactions illustrated in the reaction scheme may be carried out with esters of L-proline ($R_5$=lower alkyl) to give the products (I) and (II) wherein $R_5$ is lower alkyl. In the products wherein $R_5$ is tert-butyl the ester group may be removed in the presence of trifluoroacetic acid or aqueous trifluoroacetic acid to give the free acid derivatives of (I) and (II). Conversion of compounds of formulae (X) and (XIII) to final products (I) and (II) is achieved as set forth hereinbefore for the conversion of (VII) to (III). Derivatives which contain a thio protecting group may be converted to products (I) or (II) wherein $R_3$ is —SH by removing the protecting group under conventional conditions.

The invention will be described in greater detail in conjunction with the following specific examples.

EXAMPLE 1

1-[3-(Acetylthio)-3-(2-thenoyl)propionyl]-L-proline

A solution of 0.3 mole of thiophene in 100 ml. of nitrobenzene is added dropwise with stirring to a cooled mixture of 30 g. (0.3 mole) of succinic anhydride, 87.8 g. (0.66 mole) of aluminum chloride and 300 ml. of nitrobenzene. The mixture is cooled and stirred for 30 minutes and then allowed to stand at room temperature overnight. The mixture is poured onto ice and 50 ml. of concentrated hydrochloric acid. The nitrobenzene is removed by steam distillation. The aqueous layer is decanted and the residue is mixed with 650 ml. of water and 20 g. of sodium carbonate. The mixture is heated, mixed with diatomaceous earth and filtered. The filtrate is acidified with concentrated hydrochloric acid and the solid which separates is filtered and washed with water. Recrystallization from water gives 53% of 4-oxo-4-(2-thienyl)butyric acid, m.p. 121°–123° C.

The preceding compound (0.02 mole), 1,1'-carbonyldiimidazole (0.021 mole) and 25 ml. of tetrahydrofuran is stirred at room temperature for one hour. To the mixture is added 0.025 mole of L-proline and the mixture is stirred at room temperature for 16 hours and refluxed for one hour. The mixture is diluted with a little water and the solvent removed under reduced pressure. The residue is partitioned between dichloromethane, water and 0.04 ml. of concentrated hydrochloric acid. The dichloromethane layer is separated, washed with water, dried over magnesium sulfate and concentrated under reduced pressure to give 85% of 1-[3-(2-thenoyl)propionyl]-L-proline as crystals, m.p. 100°–102° C.

To a mixture of 0.008 mole of the preceding compound, 50 ml. of glacial acetic acid and one drop of fuming hydrogen bromide is added dropwise 0.008 mole of bromine in 25 ml. of glacial acetic acid. The mixture is stirred at room temperature overnight and the solvent removed under reduced pressure. The residue is dissolved in dichloromethane, and the solution is washed with water and dried over magnesium sulfate. The solvent is removed in vacuo to yield 53% of 1-[3-bromo-3-(2-thenoyl)propionyl]-L-proline as a glass.

A mixture of the preceding compound (0.0085 mole) in 25 ml. of ethanol is added to a mixture of 0.81 g. (0.015 mole) of sodium methoxide, 1.07 ml. (0.015 mole) of thioacetic acid and 25 ml. of ethanol. The resulting mixture is stirred at room temperature for 16 hours, the solvent is removed under reduced pressure and the residue is partitioned between dichloromethane and water containing acetic acid. The organic layer is separated, washed with water and dried over magnesium sulfate. The solvent is removed in vacuo to give an 84% yield of the product of the Example as a glass.

EXAMPLE 2

1-[3-(Acetylthio)-3-(5-bromo-2-thenoyl)propionyl]-L-proline

As described for Example 1, 0.3 mole of 2-bromothiophene is reacted with succinic anhydride to give 4-(5-bromo-2-thienyl)-4-ketobutyric acid (51%), m.p. 141°–143° C. The preceding compound is coupled to L-proline to give 1-[3-(5-bromo-2-thenoyl)propionyl]-L-proline (56%) as crystals, m.p. 166°–168° C. The preceding compound (0.008 mole) is reacted with bromine in acetic acid to yield 1-[3-bromo-3-(5-bromo-2-thenoyl)propionyl]-L-proline as a glass (97%). As for Example 1, reaction of the preceding compound with sodium thioacetate gives the product of the Example (88%) as a yellow glass.

EXAMPLE 3

1-[3-(Acetylthio)-3-(5-chloro-2-thenoyl)propionyl]-L-proline

As described for Example 1, 0.3 mole of 2-chlorothiophene is reacted with succinic anhydride to give 4-(5-chloro-2-thienyl)-4-ketobutyric acid (74%), m.p. 121°–123° C. The preceding compound is coupled to L-proline to give 1-[3-(5-chloro-2-thenoyl)propionyl]-L-proline (94%) as crystals, m.p. 131°–133° C. The above compound is reacted with bromine in acetic acid to give 1-[3-bromo-3-(5-chloro-2-thenoyl)propionyl]-L-proline as a glass. As for Example 1, reaction of the preceding compound with sodium thioacetate in ethanol gives the desired product (84%) as a glass.

EXAMPLE 4

1-[3-(Acetylthio)-3-(benzo[b]thien-3-ylcarbonyl)propionyl]-L-proline

As described in Example 1, 0.30 mole of thionaphthene is reacted with succinic anhydride to give a mixture of γ-oxo-benzo[b]thiophene-3-butyric acid, m.p. 138°–142° C. and γ-oxo-benzo[b]thiophene-2-butyric acid, m.p. 175° C.

The γ-oxo-benzo[b]thiophene-3-butyric acid is coupled to L-proline with 1,1'-carbonyldiimidazole to give 1-[3-(benzo[b]thien-3-ylcarbonyl)propionyl]-L-proline (78%) as a glass. As for Example 1, the preceding compound is reacted with bromine in acetic acid to give 1-[3-bromo-3-(benzo[b]thien-3-ylcarbonyl)propionyl]-L-proline as a glass (97%). Reaction with sodium thioacetate in ethanol gives the product (92%) of the Example as a glass.

EXAMPLE 5

1-[3-(Acetylthio)-3-(benzo[b]thien-2-ylcarbonyl)propionyl]-L-proline

As for Example 4, γ-oxo-benzo[b]thiophene-2-butyric acid is coupled to L-proline. The coupled product is brominated and reacted with sodium thioacetate to give the product of the Example as a glass.

EXAMPLE 6

1-[3-(Acetylthio)-3-(2-thenoyl)-2-methylpropionyl]-L-proline

To a mixture of 180.7 g. of p-toluenesulfonic acid in 500 ml. of tetrahydrofuran is added slowly 170 g. of morpholine. To this mixture is added 100 g. of 2-thiophenecarboxaldehyde and the resulting mixture is refluxed for 18 hours. The reaction mixture is cooled and a mixture of 65.1 g. of potassium cyanide in 100 ml. of water is added. The mixture is refluxed for 48 hours and the solvent removed under reduced pressure. The residue is dissolved in chloroform and the organic layer washed with water, sodium bisulfite solution and brine. The chloroform extract is dried over magnesium sulfate and filtered through a pad of hydrated magnesium silicate. The filtrate is concentrated and the residue is triturated with hexane to give 162 g. of α-2-thienyl-4-morpholineacetonitrile, m.p. 78°–79° C.

The preceding compound in tetrahydrofuran is reacted with methyacrylonitrile in the presence of 30% potassium hydroxide in ethanol. The product is hydrolysed with 6 N hydrochloric acid to give 3-(2-thenoyl)-2-methylpropionic acid.

The preceding compound is coupled with L-proline as described in Example 1 to give 1-[3-(2-thenoyl)-2-methylpropionyl]-L-proline (mixture of diastereomers). The [R]-1-[3-(2-thenoyl)-2-methylpropionyl]-L-proline is reacted with bromine in acetic acid and the brominated product is reacted with sodium thioacetate in acetonitrile to give a mixture of [S-(R*,S*)]-1-[3-acetylthio-3-(2-thenoyl)-2-methylpropionyl]-L-proline and [S-(R*,R*)]-1-[3-acetylthio-3-(2-thenoyl)-2-methylpropionyl]-L-proline as a glass.

EXAMPLE 7

1-[3-Acetylthio-3-(5-chloro-2-thenoyl)-2-methylpropionyl]-L-proline

As for Example 1, 3-(5-chloro-2-thenoyl)-2-methylpropionic acid is reacted with L-proline to give 1-[3-(5-chloro-2-thenoyl)-2-methylpropionyl]-L-proline. The mixture of diastereomers is separated. Bromination of [R]-1-[3-(5-chloro-2-thenoyl)-2-methylpropionyl]-L-proline and reaction of the brominated product with sodium thioacetate in acetonitrile gives a mixture of [S-(R*,S*)] and [S-(R*,R*)] isomers of the product of the Example as a glass.

Bromination of the [S]-1-[3-(5-chloro-2-thenoyl)-2-methylpropionyl]-L-proline and reaction of the brominated product with sodium thioacetate in acetonitrile gives a mixture of the [R-(R*,S*)] and [R-(R*,R*)] isomers of the product of the Example as a glass.

EXAMPLE 8

1-[3-Acetylthio-3-(3-thenoyl)-propionyl]-L-proline

As for Example 6, 99 g. of 3-thiophenecarboxaldehyde is converted to α-(3-thienyl)-4-morpholineacetonitrile (137 g.; m.p. 85°-87° C.). The preceding compound 50.5 g. is reacted with 100 ml. of ethyl acrylate in 500 ml. of tetrahydrofuran in the presence of 50 ml. of 30% potassium hydroxide in ethanol. The solvent is removed from the reaction mixture and the residue is heated with 6 N hydrochloric acid to give 3-(3-thenoyl)propionic acid. As for Example 1, the preceding compound is converted to the product of the Example to give a glass.

EXAMPLE 9

1-[3-Acetylthio-3-(3-thenoyl)-2-methylpropionyl]-L-proline

As for Example 8, α-(3-thienyl)-4-morpholineacetonitrile is reacted with methacrylonitrile and the resulting product is refluxed with 6 N hydrochloric acid to give 3-(3-thenoyl)-2-methylpropionic acid. As for Example 1, the preceding compound is coupled with L-proline to give 1-[3-(3-thenoyl)-2-methylpropionyl]-L-proline. The preceding product is reacted with bromine in acetic acid and the brominated product is reacted with sodium thioacetate in acetonitrile to give the product of the Example as a glass (mixture of diastereomers).

EXAMPLE 10

1-[3-Acetylthio-3-(5-chloro-3-thenoyl)propionyl]-L-proline

As for Example 8, 3-(5-chloro-3-thenoyl)propionic acid is coupled to L-proline with 1,1'-carbonyldiimidazole. The coupled product is reacted with bromine in acetic acid and the brominated derivative is reacted with sodium thioacetate in acetonitrile to give the product of the Example as a glass.

EXAMPLE 11

1-[3-Acetylthio-3-(2-pyridylcarbonyl)propionyl]-L-proline

To a solution of 3.58 g. of γ-oxo-2-pyridinebutyric acid, m.p. 67°-80° C. and 2.30 g. of N-hydroxysuccinimide in 25 ml. of dioxane is added a solution of 4.12 g. of N,N-dicyclohexylcarbodiimide in 25 ml. of dioxane. The mixture is stirred for 18 hours at room temperature and filtered. The filtrate is concentrated under reduced pressure. The residue is triturated with hexane to give 5.3 g. of tan solid. The solid is recrystallized by dissolving in 50 ml. of methylene chloride. The solution is diluted with 50 ml. of hexane, then chilled and filtered to give 3.1 g. of γ-oxo-2-pyridinebutyric acid, N-hydroxysuccinimide ester as crystals, m.p. 143°-145° C.

The preceding compound (3.1 g.) as a slurry in 60 ml. of ethanol is added to a mixture of 1.9 g. of L-proline and 2.75 g. of sodium bicarbonate in 60 ml. of water. The mixture is stirred at room temperature for 48 hours, then concentrated to ½ its volume. The mixture is chilled (ice bath) and acidified by dropwise addition of concentrated hydrochloric acid. The mixture is extracted with ethyl acetate. The extract is dried over magnesium sulfate and concentrated to give 1.06 g. of 1-[3-(2-pyridylcarbonyl)propionyl]-L-proline as a gum. The preceding compound (0.276 g.) is dissolved in 5 ml. of glacial acetic acid and 0.16 g. of bromine in 2 ml. of acetic acid is added. The mixture is stirred at room temperature for 2 hours and the solvent removed. The residue is reacted with sodium thioacetate in acetonitrile for 4 hours to give the product of the Example as a glass.

EXAMPLE 12

1-[3-Acetylthio-3-(3-pyridylcarbonyl)propionyl]-L-proline

As for Example 11, γ-oxo-3-pyridinebutyric acid is coupled to L-proline to give 1-[3-(3-pyridylcarbonyl)propionyl]-L-proline.

Bromination with bromine in acetic acid and reaction of the brominated derivative with sodium thioacetate in acetonitrile gives the product of the Example as a glass.

EXAMPLE 13

1-[3-Acetylthio-3-(2-pyridylcarbonyl)propionyl]-L-proline, pyridine-1-oxide

As for Example 11, γ-oxo-2-pyridinebutyric acid, pyridine-1-oxide is coupled to L-proline to give 1-[3-(2-pyridylcarbonyl)propionyl]-L-proline, pyridine-1-oxide. Reaction of the preceding compound with bromine in acetic acid and reaction of the brominated compound with sodium thioacetate in acetonitrile gives the product of the Example as a glass.

EXAMPLE 14

1-[3-Acetylthio-3-(3-indolylcarbonyl)propionyl]-L-proline

As for Example 1, 4-oxo-4-(3-indolyl)butyric acid (0.1 mole) is coupled to L-proline to give 1-[3-(3-indolylcarbonyl)propionyl]-L-proline. The preceding compound is reacted with bromine in acetic acid and the brominated derivative is reacted with sodium thioacetate in acetonitrile to give the product of the Example as a glass.

EXAMPLE 15

1-[3-Acetylthio-3-(1-methyl-3-indolylcarbonyl)propionyl]-L-proline

As for Example 11, the N-hydroxysuccinimide ester of 3-(1-methyl-3-indolylcarbonyl)propionic acid is prepared and coupled to L-proline to give 1-[3-(1-methyl-3-indolylcarbonyl)propionyl]-L-proline. The preceding compound is reacted with bromine in acetic acid and the brominated derivative reacted with sodium thioacetate in acetonitrile to give the product of the Example as a glass.

EXAMPLE 16

1-[3-Acetylthio-3-(3-pyrazolylcarbonyl)propionyl]-L-proline

Substitution of 3-pyrazolecarboxaldehyde for 2-thiophenecarboxaldehyde in Example 6 gives the product of the Example.

EXAMPLE 17

1-[3-Acetylthio-3-(5-methyl-3-pyrazolylcarbonyl)propionyl]-L-proline

Substitution of 5-methyl-3-pyrazolecarboxaldehyde for 2-thiophenecarboxaldehyde in Example 6 gives the product of the Example.

EXAMPLE 18

1-[3-Acetylthio-3-(4-pyrimidylcarbonyl)propionyl]-L-proline

Substitution of 4-pyrimidinecarboxaldehyde for 2-thiophenecarboxaldehyde in Example 6 gives the product of the Example.

EXAMPLE 19

1-[3-Acetylthio-3-(2-methyl-4-pyrimidylcarbonyl)propionyl]-L-proline

Substitution of 2-methyl-4-pyrimidinecarboxaldehyde for 2-thiophenecarboxaldehyde in Example 6 gives the product of the Example.

EXAMPLE 20

1-[3-Acetylthio-3-(1-methyl-2-imidazolylcarbonyl)propionyl]-L-proline

Substitution of 1-methyl-2-imidazolecarboxaldehyde for 2-thiophenecarboxaldehyde in Example 6 gives the product of the Example as a glass.

EXAMPLE 21

1-[3-(Benzoylthio)-3-(2-thenoyl)propionyl]-L-proline

As for Example 1, 1-[3-bromo-3-(2-thenoyl)propionyl]-L-proline (0.0085 mole) in 25 ml. of acetonitrile is added to a mixture of 0.015 mole of sodium methoxide and 0.015 mole of thiobenzoic acid in 25 ml. of acetonitrile. The mixture is stirred at room temperature for 16 hours, one ml. of acetic acid is added and the solvent removed under reduced pressure. The residue is partitioned between dichloromethane and water containing acetic acid. The organic layer is separated, washed with water, dried over magnesium sulfate and the solvent removed under reduced pressure to give the product of the Example as a pale yellow glass.

EXAMPLE 22

1-[3-(Benzoylthio)-3-(benzo[b]thien-3-ylcarbonyl)propionyl]-L-proline

As for Example 21, 1-[3-bromo-3-(benzo[b]thien-3-ylcarbonyl)propionyl]-L-proline (0.01 mole) in 25 ml. of acetonitrile is added to a mixture of 0.01 mole of sodium methoxide and 0.015 mole of thiobenzoic acid in 25 ml. of acetonitrile. The mixture is stirred at room temperature for 16 hours, one ml. of acetic acid is added and the solvent is evaporated in vacuo. The residue is partitioned between dichloromethane and water containing acetic acid. The organic layer is separated, washed with water and dried over magnesium sulfate. The solvent is removed in vacuo to give the product of the Example as a yellow glass.

EXAMPLE 23

1-[3-(Benzoylthio)-3-(5-chloro-2-thenoyl)propionyl]-L-proline

As for Example 21, 0.01 mole of 1-[3-bromo-3-(5-chloro-2-thenoyl)propionyl]-L-proline is reacted with sodium thiobenzoate for 16 hours in acetonitrile to give the product of the Example as a glass.

EXAMPLE 24

1-[3-(Benzoylthio)-3-(1-methyl-2-pyrrolylcarbonyl)propionyl]-L-proline

As for Example 6, 1-methyl-2-pyrrolecarboxaldehyde is converted to α-(1-methyl-2-pyrrolyl)-4-morpholineacetonitrile. The preceding compound is reacted with ethyl acrylate and the resulting 1,4-addition product is heated at 100° C. with 6 N hydrochloric acid to give 3-(1-methyl-2-pyrrolylcarbonyl)propionic acid.

As for Example 1, the preceding compound is coupled to L-proline to give 1-[3-(1-methyl-2-pyrrolylcarbonyl)propionyl]-L-proline. The preceding compound (0.01 mole) is brominated with bromine (0.011 mole) in acetic acid and the resulting 1-[3-bromo-(1-methyl-2-pyrrolylcarbonyl)propionyl]-L-proline (0.01 mole) is reacted with sodium thiobenzoate as for Example 21 to give the product of the Example as a glass.

EXAMPLE 25

1-[3-(Acetylthio)-3-(2-thenoyl)propionyl]-L-proline, methyl ester

Substituting L-proline, methyl ester for L-proline in Example 1 gives the product of the Example as a glass.

EXAMPLE 26

1-[3-(Acetylthio)-3-(5-chloro-2-thenoyl)propionyl]-L-proline, t-butyl ester

Substituting the t-butyl ester of L-proline for L-proline in Example 3 gives the product of the Example as a glass.

EXAMPLE 27

1-[2-(Acetylthio)-3-(2-thenoyl)propionyl]-L-proline

As for Example 1, 3-(2-thenoyl)acrylic acid (0.01 mole) is coupled to L-proline (0.01 mole) with N,N'-carbonyldiimidazole (0.011 mole) in tetrahydrofuran to give 1-[3-(2-thenoyl)acryloyl]-L-proline.

A mixture of the preceding compound (0.01 mole) and thioacetic acid (0.03 mole) in carbon tetrachloride is refluxed for 3 hours. The solvent is removed in vacuo to give the product of the Example as a glass.

EXAMPLE 28

1-[2-Acetylthio)-3-(benzo[b]thien-3-ylcarbonyl)propionyl]-L-proline

As for Example 1, 3-(benzo[b]thien-3-ylcarbonyl)acrylic acid (0.01 mole) is coupled to L-proline (0.01 mole) with N,N'-carbonyldiimidazole in tetrahydrofuran to give 1-[3-(benzo[b]thien-3-ylcarbonyl)acryloyl]-L-proline.

A mixture of the preceding compound (0.01 mole) and thioacetic acid (0.03 mole) in carbon tetrachloride is refluxed for 2 hours. The solvent is removed in vacuo to give the product of the Example as a glass.

EXAMPLE 29

1-[2-Acetylthio-3-(3-pyridylcarbonyl)propionyl]-L-proline

As for Example 27, 3-(3-pyridylcarbonyl)acrylic acid (0.01 mole) is reacted with N,N'-carbonyldiimidazole (0.011 mole) in tetrahydrofuran and to the mixture is added 0.011 mole of L-proline. The mixture is refluxed 16 hours and the solvent removed under reduced pressure. The mixture is partitioned between dichloromethane and water containing acetic acid. The organic layer is separated, washed with water and dried over magnesium sulfate. The solvent is removed in vacuo to yield 1-[3-(3-pyridylcarbonyl)acryloyl]-L-proline. The preceding compound is dissolved in carbon tetrachloride and 0.03 mole of thioacetic acid is added. The mixture is heated 3 hours and the solvent is removed in vacuo to give the product of the Example as a glass.

EXAMPLE 30

1-[2-Acetylthio-3-(1-methyl-3-indolylcarbonyl)propionyl]-L-proline

As for Example 29, 3-(1-methyl-3-indolylcarbonyl)acrylic acid is coupled to L-proline to give 1-[3-(1-methyl-3-indolylcarbonyl)acryloyl]-L-proline.

A mixture of 0.01 mole of the preceding compound, and 0.03 mole of thioacetic acid in methanol is refluxed for 4 hours. The solvent is removed to give the product of the Example as a glass.

EXAMPLE 31

1-[2-Acetylthio-3-(1-methyl-4-pyrazolylcarbonyl)propionyl]-L-proline

As for Example 29, 3-(1-methyl-4-pyrazolylcarbonyl)acrylic acid is coupled to L-proline and the resulting 1-[3-(1-methyl-4-pyrazolylcarbonyl)acryloyl]-L-proline is reacted with thioacetic acid to give the product of the Example as a glass.

EXAMPLE 32

1-[3-Acetyl-3-(2-quinolylcarbonyl)propionyl]-L-proline

As for Example 6, 3-(2-quinolylcarbonyl)propionic acid (0.01 mole) is coupled to L-proline (0.011 mole) with 1,1'-carbonyldiimidazole (0.01 mole) in tetrahydrofuran to give 1-[3-(2-quinolylcarbonyl)propionyl]-L-proline. Bromination of the preceding compound and reaction of the resulting compound with sodium thioacetate gives the product of the Example.

EXAMPLE 33

1-[3-Acetylthio-4-(2-thenoyl)butyryl]-L-proline

To a mixture of 0.01 mole of 4-(2-thenoyl)crotonic acid in 50 ml. of tetrahydrofuran is added 0.011 mole of N,N'-carbonyldiimidazole. After stirring for 2 hours, L-proline (0.01 mole) is added and the mixture is stirred for 24 hours at room temperature and refluxed for one hour to give 1-[4-(2-thenoyl)crotonyl]-L-proline.

A mixture of the preceding compound and 0.03 moles of thioacetic acid in dichloromethane is refluxed for 10 hours to give the product of the Example as a glass.

EXAMPLE 34

1-[3-Acetylthio-4-(2-furoyl)butyryl]-L-proline

To a mixture of 0.02 moles of 4-(2-furoyl)crotonic acid in 100 ml. of tetrahydrofuran is added 0.022 moles of N,N'-carbonyldiimidazole. The mixture is stirred for 3 hours at room temperature and 0.021 moles of L-proline are added. The mixture is refluxed 2 hours and stirred at room temperature for 16 hours to give 1-[4-(2-furoyl)crotonyl]-L-proline.

A mixture of the preceding compound and 0.04 moles of thioacetic acid in dichloromethane is refluxed for 10 hours to give the product of the Example as a glass.

EXAMPLE 35

1-[3-Acetylthio-3-(benzo[b]thien-2-ylcarbonyl)-2-methylpropionyl]-L-proline

To a solution of 2.68 g. (0.020 mole) of benzo[b]thiophene in 40 ml. of ether cooled at −20° C. is added 0.020 moles of n-butyl lithium (2.54 N solution in hexane). The mixture is stirred at −20° C. for 15 minutes, then is allowed to warm to room temperature. Then 2.70 g. (0.020 mole) of N-methylformamilide is added and the mixture is stirred for 24 hours. The reaction is quenched with water and the mixture is treated with saturated sodium bisulfite solution. The bisulfite addition product is collected by filtration. The wet cake is slurried in water and decomposed by the addition of solid sodium carbonate. The mixture is filtered and the solid is washed with water and dried to give 1.75 g. of benzo[b]thiophene-2-carboxaldehyde.

To a solution of 47.0 g. of the preceding compound (prepared as described above) in 250 ml. of tetrahydrofuran is added 60.5 g. of p-toluenesulfonic acid hydrate followed by 55.0 g. of morpholine in 60 ml. of tetrahydrofuran. The reaction mixture is refluxed for one hour and cooled to 40° C. A slurry of 20.4 g. of potassium cyanide in 16 ml. of water is added and the mixture is refluxed for an additional 20 hours. The solvent is removed in vacuo and the residue is partitioned between chloroform and water. The organic layer is washed with saturated sodium bisulfite solution, then with brine, dried over magnesium sulfate, treated with activated charcoal, filtered and concentrated to give a brown oil which is crystallized from chloroform-hexane to give 62.1 g. of α-(benzo[b]thien-2-yl)-4-morpholineacetonitrile.

To a solution of 56.8 g. of the preceding compound in 40 ml. of tetrahydrofuran is added 5 ml. of 30% potassium hydroxide in methanol, the solution turns dark brown. Then 22.0 ml. of methacrylonitrile is added (exothermic reaction) with stirring and the solution darkens further to a dark violet. Stirring is continued at ambient temperature for 20 hours. The mixture is concentrated in vacuo to a brown-violet oil which is taken up in chloroform and passed through hydrous magnesium silicate with chloroform as eluent. The eluent is concentrated and the residue is crystallized from cyclohexane/dichloromethane to give 60.9 g. of 4-[benzo[b]thien-2-yl]-2-methyl-4-morpholinoglutaronitrile as a solid.

A mixture of 16.98 g. of the above compound, 120 ml. of acetic acid and 8.0 ml. of water is heated at 100° C. for 18 hours. The mixture is concentrated in vacuo and the residue is dissolved in dichloromethane. This solution is passed through hydrous magnesium silicate with dichloromethane as eluent. The eluent is evaporated in vacuo and the residue is crystallized from chloroform-hexane to give 8.60 g. of 3-(benzo[b]thien-2-ylcarbonyl)-2-methylpropionitrile.

A mixture of 21.5 g. of the preceding compound (prepared as described) and 400 ml. of 6 N hydrochloric acid is refluxed for 24 hours. The mixture is cooled and then extracted with chloroform. The extracts are combined and passed through hydrous magnesium silicate with chloroform as eluent. The eluent is evaporated to give 21.1 g. of 3-(benzo[b]thien-2-ylcarbonyl)-2-methylpropionic acid.

To a solution of 19.67 g. of the above compound in 400 ml. of tetrahydrofuran is added 13.49 g. of N,N'-carbonyldiimidazole. The mixture is stirred for 4 hours, then 9.11 g. of L-proline is added and stirring is continued for 19 hours longer at room temperature. The mixture is concentrated in vacuo and the residue is partitioned between chloroform and water. The organic layer is washed with 2 N hydrochloric acid, dried over anhydrous sodium sulfate and evaporated in vacuo to give 1.83 g. of product as a viscous gum. The above aqueous layer is reextracted with chloroform to obtain an additional 2.39 g. of product to give a total yield of 4.22 g. of 1-[3-(benzo[b]thien-2-ylcarbonyl)-2-methylpropionyl]-L-proline.

To a solution of 4.22 g. of the preceding compound in 60 ml. of glacial acetic acid is added 2 drops of fuming hydrogen bromide, followed by the dropwise addition of a solution of 1.95 g. of bromine in 10 ml. of glacial acetic acid over a period of 25 minutes. The mixture is stirred for an additional 3 hours then the solvent is removed in vacuo. The residue is dissolved in 10 ml. of ethanol and is added to a solution of 0.95 g. of thiolacetic acid and 0.69 g. of potassium hydroxide in 10 ml. of ethanol. This mixture is stirred at room temperature for 3 hours then is filtered through diatomaceous earth. The filtrate is evaporated in vacuo and the residue is partitioned between dichloromethane and water containing a few drops of acetic acid. The organic layer is washed with water, dried over anhydrous sodium sulfate and evaporated to give 0.21 g. of the product of the Example as a glass.

EXAMPLE 36

1-[3-Acetylthio-3-(2-furoyl)propionyl]-L-proline

To a mixture of 82.19 g. of 2-acetylfuran, 60.8 g. of dimethylamine hydrochloride and 22.4 g. of paraformaldehyde in 225 ml. of ethanol is added 2.0 ml. of concentrated hydrochloric acid. The mixture is refluxed for 15 minutes, an additional 11.2 g. of paraformaldehyde is added and the reaction mixture is refluxed for another ½ hour. After standing at room temperature for 16 hours the reaction mixture is filtered. The solid is washed twice with 50 ml. of alcohol to give 47.2 g. of 3-dimethylamino-1-(2-furyl)-1-propanone.

The preceding compound (47.2 g.) is dissolved in 1.6 liters of water. To this solution is added 30.2 g. of potassium cyanide. The resulting yellow solution is refluxed for ½ hour, cooled to room temperature and extracted with four 200 ml. portions of chloroform. The combined extract is dried over anhydrous sodium sulfate, filtered and evaporated in vacuo to give a brown solid. The solid is recrystallized from ethanol with the aid of activated carbon to give 5.49 g. of 3-(2-furoyl)propionitrile as a brownish solid.

The above product (5.49 g.) is hydrolyzed by refluxing with 100 ml. of 6 N hydrochloric acid for one hour. To the hot solution is added one gram of activated carbon. The mixture is filtered hot and the filtrate is cooled in a refrigerator for 16 hours. The precipitate formed is collected and washed with water to give 3.52 g. of 3-(2-furoyl)propionic acid.

A mixture of the preceding compound (3.52 g.), 2.41 g. of N-hydroxysuccinimide and 4.32 g. of dicyclohexylcarbodiimide in 50 ml. of p-dioxane is stirred at room temperature for 20 hours. The mixture is filtered and the fine white precipitate is washed with dioxane. The combined filtrate and wash is evaporated in vacuo and the residue is crystallized from hexane-dichloromethane to give 4.0 g. of the N-hydroxysuccinimide ester of 3-(2-furoyl)propionic acid as a yellow-brown solid.

To a solution of 2.57 g. of L-proline and 3.75 g. of sodium bicarbonate in 85 ml. of water is added a slurry of 4.0 g. of the preceding compound in 85 ml. of ethanol. The reaction mixture is stirred at room temperature for 21 hours. The solution is concentrated to ½ volume in vacuo, then is acidified with hydrochloric acid and extracted with four 50 ml. portions of dichloromethane. The combined organic layer is dried over anhydrous sodium sulfate, filtered and evaporated in vacuo to give a yellow-orange oil. The oil is crystallized from ether to give 1.8 g. of 1-[3-(2-furoyl)propionyl]-L-proline.

To a stirred solution of 1.8 g. of the preceding product in 35 ml. of glacial acetic acid at room temperature is added one drop of fuming hydrogen bromide, followed by the dropwise addition of a solution of 1.09 g. of bromine in 15 ml. of glacial acetic acid over a 30 minute period. The reaction mixture is completely decolorized after 40 minutes and is stirred for an additional 3 hours. The solution is evaporated in vacuo and the residue is chromatographed in a conventional manner on preparative thin layer chromatography plates to give 1.22 g. of 1-[3-bromo-3-(furoyl)propionyl]-L-proline.

To a solution of 0.35 g. of thiolacetic acid in 5 ml. of ethanol is added 0.26 g. of potassium hydroxide. To this solution is added with stirring 1.22 g. of the above compound in 5.0 ml. of ethanol. The mixture is stirred for one hour and filtered. The filtrate is evaporated to give an orange oil. Further evaporation under high vacuum gives the product of the Example as a glass.

EXAMPLE 37

1-[3-Acetylthio-3-(2-benzofuranylcarbonyl)propionyl]-L-proline

To a solution of 50.0 g. of 2-benzofuranyl methyl ketone in 200 ml. of glacial acetic acid is added 2.0 ml. of fuming hydrobromic acid (48%), followed by the dropwise addition of a solution of 49.9 g. of bromine (16 ml.) in 30 ml. of acetic acid over a 2½ hour period. The temperature of the reaction mixture is maintained at 80° C. during this addition and is kept at 80° C. for an additional hour, then is allowed to cool gradually to room temperature. The reaction mixture is added to 2 liters of water. The aqueous layer is decanted and the residue is chromatographed on a short column of silica gel. The column is eluted with dichloromethane. The eluent is evaporated to give a residue. The residue is crystallized from ethanol:isopropanol (3:17). As the hot solution cools an oily solid separates. The supernatant is decanted and allowed to stand to crystallize the product, 17.01 g. of 2-benzofuranyl bromomethyl ketone.

To a stirred solution of 7.41 g. of diethylmalonate in 100 ml. of ethanol is added 1.06 g. of sodium. The mixture is stirred until the sodium has reacted. The mixture is heated to 80° C. and 11.06 g. of 2-benzofuranyl bromomethyl ketone in 100 ml. of hot ethanol is added in one portion. The mixture is refluxed for 2 hours and concentrated in vacuo. The residue is dissolved in ether and is passed through a short column of hydrous magnesium silicate. The column is eluted with ether. The ether is evaporated to give a residue. To the residue is added 200 ml. of water, 100 ml. of methanol and 60 ml. of 10 N sodium hydroxide. This mixture is refluxed 4 hours and cooled to room temperature. The aqueous layer is decanted, neutralized with concentrated hydrochloric acid and heated for 2 hours on a hot plate. The mixture is allowed to cool to separate a solid. The solid is collected, washed with water and air dried. The solid is heated to its melting point (160° C.) where it decarboxylates. The residue is crystallized with a small amount of acetone to give 0.98 g. of 3-(2-benzofuranylcarbonyl)propionic acid.

A mixture of 1.72 g. of the preceding compound (prepared as described), 0.91 g. of N-hydroxysuccinimide, 1.63 g. of dicyclohexylcarbodiimide and 50 ml. of p-dioxane is stirred at room temperature for 20 hours. The resulting solid is filtered off and washed with 20 ml. of p-dioxane. The combined filtrate and wash is evaporated to give a brown-orange oil. The oil is crystallized with dichloromethane/hexane to give 1.76 g. of N-hydroxysuccinimide ester of 3-(2-benzofuranylcarbonyl)propionic acid.

To a solution of 1.50 g. of the above compound in 25 ml. of ethanol is added a solution of 0.8 g. of L-proline and 1.17 g. of sodium bicarbonate in 25 ml. of water. The mixture is stirred at room temperature for 20 hours. The organic solvent is removed in vacuo and the resulting aqueous slurry is diluted with 75 ml. of water, acidified to pH 2.5 with concentrated hydrochloric acid and extracted with dichloromethane. The organic layer is separated, dried over anhydrous sodium sulfate and evaporated to give 1.0 g. of 1-[3-(2-benzofuranylcarbonyl)propionyl]-L-proline as a glass.

To a solution of 0.76 g. of the preceding compound in 12 ml. of glacial acetic acid is added one drop of hydrogen bromide (48%), followed by the dropwise addition of a solution of 0.39 g. of bromine in 5 ml. of glacial acetic acid over a 15 minute period. The mixture is stirred at room temperature for 28 hours. The solvent is removed in vacuo and the residue is chromatographed in a conventional manner using preparative thin layer chromatography, developing with ethylacetate:hexane (3:1) with 2% glacial acetic acid. The major band is collected and extracted with tetrahydrofuran to give 0.34 g. of 1-[3-bromo-3-(2-benzofuranylcarbonyl)propionyl]-L-proline.

The preceding compound (0.34 g.) is added to a stirred solution of 63 mg. of potassium hydroxide and 85 mg. of thiolacetic acid in 2.0 ml. of ethanol. The mixture is stirred at room temperature for 3 hours, then is filtered. The solid is washed with 2.0 ml. of ethanol. The combined ethanol filtrate and wash is evaporated in vacuo and the residue is partitioned between dichloromethane and water. The organic layer is washed with water, dried over anhydrous sodium sulfate and filtered. The filtrate is evaporated in vacuo to give 120 mg. of the product of the Example as a glass.

We claim:
1. A compound selected from the group consisting of those of the formulae:

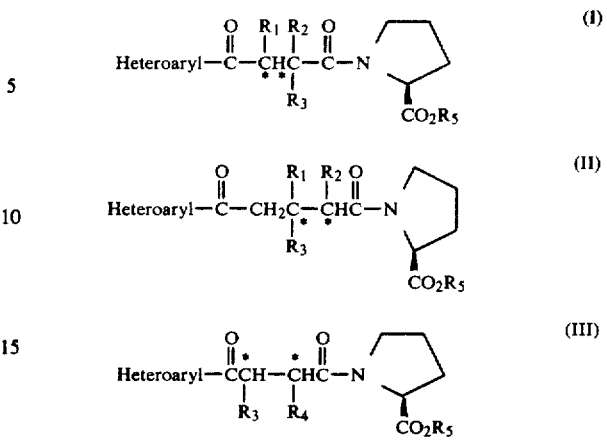

wherein $R_1$ is hydrogen or alkyl having 1–3 carbon atoms; $R_2$ is hydrogen or alkyl having 1–3 carbon atoms; $R_3$ is mercapto, formylthio, benzoylthio, alkanoylthio having 2–4 carbon atoms or moieties of the formulae: $-S-CO_2CH_2C_6H_5$, $-S-CO_2R_5$, $-S-CH_2CO_2R_5$ or $-S-CO-N(R_5)2$; $R_4$ is hydrogen or alkyl having 1–4 carbon atoms; $R_5$ is hydrogen or alkyl having 1–4 carbon atoms; and Heteroaryl is selected from the group consisting of moieties of the formulae:

wherein $R_6$ is hydrogen, fluoro, chloro, bromo or alkyl having 1–4 carbon atoms; and the pharmacologically acceptable cationic salts thereof when $R_5$ is hydrogen.

2. The compound according to claim 1, formula (III) thereof, wherein $R_3$ is acetylthio, $R_4$ and $R_5$ are both hydrogen, and Heteroaryl is 2-benzofuranyl; 1-[3-(acetylthio)-3-(2-benzofuranylcarbonyl)propionyl]-L-proline.

3. The compound according to claim 1, formula (III) thereof, wherein $R_3$ is acetylthio, $R_4$ and $R_5$ are both hydrogen, and Heteroaryl is 3-benzofuranyl; 1-[3-(acetylthio)-3-(3-benzofuranylcarbonyl)propionyl]-L-proline.

4. The compound according to claim 1, formula (III) thereof, wherein $R_3$ is benzoylthio, $R_4$ and $R_5$ are both hydrogen, and Heteroaryl is 2-benzofuranyl; 1-[3-(benzoylthio)-3-(2-benzofuranylcarbonyl)propionyl]-L-proline.

5. The compound according to claim 1, formula (I) thereof, wherein $R_1$, $R_2$, and $R_5$ are all hydrogen, $R_3$ is acetylthio, and Heteroaryl is 3-benzofuranyl; 1-[2-(acetylthio)-3-(3-benzofuranylcarbonyl)propionyl]-L-proline.

6. The compound according to claim 1, formula (III) thereof, wherein $R_3$ is acetylthio, $R_4$ is methyl, $R_5$ is hydrogen, and Heteroaryl is 2-benzofuranyl; 1-[3-(acetylthio)-3-(2-benzofuranylcarbonyl)-2-methylpropionyl]-L-proline.

7. The compound according to claim 1, formula (I) thereof, wherein $R_1$, $R_2$, and $R_5$ are all methyl, $R_3$ is mercapto, and Heteroaryl is 3-benzofuranyl; 1-[2-(mercapto)-3-(3-benzofuranylcarbonyl)-2,3-dimethylpropionyl]-L-proline, methyl ester.

8. The compound according to claim 1, formula (II) thereof, wherein $R_1$, $R_2$, and $R_5$ are all ethyl, $R_3$ is formylthio, and Heteroaryl is 2-benzofuranyl; 1-[3-(formylthio)-4-(2-benzofuranylcarbonyl)-2,3-diethylbutyryl]-L-proline, ethyl ester.

9. The compound according to claim 1, formula (II) thereof, wherein $R_1$, $R_2$, and $R_5$ are all hydrogen, $R_3$ is benzoylthio, and Heteroaryl is 3-benzofuranyl; 1-[3-(benzoylthio)-4-(3-benzofuranylcarbonyl)butyryl]-L-proline.

10. The compound according to claim 1, formula (I) thereof, wherein $R_1$, $R_2$, and $R_5$ are all hydrogen, $R_3$ is benzoylthio, and Heteroaryl is 2-benzofuranyl; 1-[2-(benzoylthio)-3-(2-benzofuranylcarbonyl)propionyl]-L-proline.

* * * * *